United States Patent
Kolter et al.

(10) Patent No.: US 10,668,156 B2
(45) Date of Patent: Jun. 2, 2020

(54) ACTIVE-INGREDIENT-CONTAINING SOLID DISPERSIONS BASED ON DIETHYLAMINOETHYL METHACRYLATE COPOLYMERS

(71) Applicant: BASF SE, Ludwigshafen (DE)

(72) Inventors: Karl Kolter, Limburgerhof (DE); Maximilian Angel, Schifferstadt (DE); Matthias Karl, Mannheim (DE); Silke Gebert, Grünstadt (DE); Michael Klemens Mueller, Haßloch (DE)

(73) Assignee: BASF SE, Ludwigshafen (DE)

(*) Notice: Subject to any disclaimer, the term of this patent is extended or adjusted under 35 U.S.C. 154(b) by 700 days.

(21) Appl. No.: 13/919,092

(22) Filed: Jun. 17, 2013

(65) Prior Publication Data
US 2013/0345320 A1    Dec. 26, 2013

Related U.S. Application Data

(60) Provisional application No. 61/662,942, filed on Jun. 22, 2012.

(51) Int. Cl.
*A61K 47/32* (2006.01)
*A61K 9/16* (2006.01)
*A61K 9/14* (2006.01)

(52) U.S. Cl.
CPC .............. *A61K 47/32* (2013.01); *A61K 9/146* (2013.01); *A61K 9/1635* (2013.01)

(58) Field of Classification Search
CPC ............................... A61K 47/32; A61K 9/1635
See application file for complete search history.

(56) References Cited

U.S. PATENT DOCUMENTS

| | | |
|---|---|---|
| 6,624,210 B1 | 9/2003 | Petereit et al. |
| 7,160,558 B2 | 1/2007 | Petereit et al. |
| 7,175,857 B2 | 2/2007 | Petereit et al. |
| 2003/0064036 A1 | 4/2003 | Petereit et al. |
| 2004/0249035 A1 | 12/2004 | Petereit et al. |
| 2011/0033532 A1* | 2/2011 | Angel .................. A61K 9/2018 424/465 |
| 2012/0059054 A1 | 3/2012 | Kolter et al. |
| 2012/0076834 A1 | 3/2012 | Kolter et al. |
| 2012/0219694 A1 | 8/2012 | Kolter et al. |
| 2012/0219695 A1 | 8/2012 | Kolter et al. |
| 2013/0236505 A1 | 9/2013 | Kolter et al. |
| 2013/0345320 A1 | 12/2013 | Kolter et al. |

FOREIGN PATENT DOCUMENTS

| | | |
|---|---|---|
| WO | WO-00/05307 | 2/2000 |
| WO | WO-02/067906 | 9/2002 |
| WO | WO-2004/019918 | 3/2004 |
| WO | WO-2007/115381 | 10/2007 |
| WO | WO-2009/016258 | 2/2009 |
| WO | WO-2010/015713 | 2/2010 |
| WO | WO-2012/031934 | 3/2012 |
| WO | WO-2012/041788 | 4/2012 |
| WO | WO-2012/116940 | 9/2012 |
| WO | WO-2012/116941 | 9/2012 |
| WO | WO-2013/131986 | 9/2013 |

OTHER PUBLICATIONS

"BASF"—Kollicoat Smartseal 30D presentation (http://ipecamericas.org/sites/default/files/ctools/efl11May10HallB-3NigelLangleyBASF.pdf); dated Oct. 2010, accessed May 7, 2014.*
Kang et al. "Comparison of the Biological Activity between Ultrafine and Fine Titanium Dioxide Particles in RAW 264.7 Cells Associated with Oxidative Stress" J Toxicol Env Heal A 2008, 71, p. 478-485.*
"BASF"—Kollicoat Smartseal 30D presentation (http://ipecamericas.org/sites/default/files/ctools/efl11May10HallB-3NigelLangleyBASF.pdf); dated Oct. 2010, accessed May 7, 2014.*
Papageorgiou, V.P. et al. "The Chemistry and Biology of Alkannin, Shikonin, and Related Naphthazarin Natural Products" Angew. Chem. Int. Ed. 1999, 38, 270-300.*
PubChem "Alkannin" (https://pubchem.ncbi.nlm.nih.gov/compound/72521) accessed Jul. 13, 2016, pp. 1-36.*
"BASF"—Kollicoat Smartseal 30D presentation (http://ipecamericas.org/sites/default/files/ctools/efl11May10HallB-3NigelLangleyBASF.pdf); dated Oct. 2010, accessed May 7, 2014 (Year: 2014).*
Papageorgiou, V.P. et al. "The Chemistry and Biology of Alkannin, Shikonin, and Related Naphthazarin Natural Products" Angew. Chem. Int. Ed. 1999, 38, 270-300 (Year: 1999).*
Alkannin definition (http://www.dictionary.com/browse/alkannin), accessed Feb. 1, 2017, p. 1. (Year: 2017).*
Lobmann, K. et al. "Coamorphous Drug Systems: Enhanced Physical Stability and Dissolution Rate of Indomethacin and Naproxen" Mol. Pharmaceutics 2011, 8, 1919-1928 (Year: 2011).*
PCT International Search Report in PCT/EP2013/061972, dated Oct. 21, 2013, 3 pages.
Jung, Jae-Young, et al., Enhanced solubility and dissolution rate of itraconzaole by a solid dispersion technique, International Journal of Pharmaceutics 187 1999, 209-218.
Leuner, Christian, et al., Improving Drug Solubility for Oral Delivery Using Solid Dispersions, European Journal of Pharmaceutics and Biopharmaceutics, vol. 50 2000, 47-60.
Six, Karel, et al., Increased Physical Stability and Improved Dissolution Properties of Itraconazole, a Class II Drug, by Solid Dispersions that Combine Fast- and Slow-Dissolving Polymers, Journal of Pharmaceutical Sciences, vol. 93, No. 1 Jan. 2004, 124-131.

* cited by examiner

*Primary Examiner* — Andrew S Rosenthal
(74) *Attorney, Agent, or Firm* — Marshall, Gerstein & Borun LLP (57) ABSTRACT

Described are solid dispersions of hydrophobic active ingredients and cationic copolymers of N,N-diethylaminoethyl methacrylate and methyl methacrylate in a weight ratio of the monomers of from 35:65 to 55:45. Also described are the preparation and use of such solid dispersions for pharmaceutical dosage forms.

16 Claims, 2 Drawing Sheets

Figure 1 n=3; mean± sd

ACTIVE-INGREDIENT-CONTAINING SOLID DISPERSIONS BASED ON DIETHYLAMINOETHYL METHACRYLATE COPOLYMERS

CROSS-REFERENCE TO RELATED APPLICATIONS

This application claims priority to Provisional Application 61/662,942, filed on Jun. 22, 2012, the content of which is hereby incorporated by reference in its entirety.

TECHNICAL FIELD

The present invention relates to solid dispersions of hydrophobic active ingredients for pharmaceutical dosage forms based on a cationic copolymer of N,N-diethylaminoethyl methacrylate and methyl methacrylate in a weight ratio of the monomers of from 35:65 to 55:45. The present invention further relates to the preparation and use of such solid dispersions for pharmaceutical dosage forms.

BACKGROUND

WO 00/05307, WO 02/067906, and WO 2004/019918 describe cationic aminoalkyl acrylate copolymers and the use thereof as coatings and binders.

WO 2009/016258 discloses the preparation of the aqueous polymer dispersions of cationic polymers based on N,N-diethylaminoethyl methacrylate as are used according to the invention and the use thereof for coating drugs.

The term "solid dispersion" describes systems in which the active ingredient is embedded in the polymer matrix in the form of microdisperse domains. Such systems are true solid dispersions in the sense that the disperse phase and the continuous phase are solid phases.

Furthermore, the term "solid dispersion" also comprises so-called "solid solutions" in which the active ingredient is present in molecularly disperse form embedded in the solid polymer phase (the matrix). Such solid solutions lead, for example when used in solid pharmaceutical presentation forms of a sparingly soluble active ingredient, to an improved release of the active ingredient. An important requirement of such solid solutions is that they are stable, i.e. that the active ingredient does not crystallize out, even upon storage over a prolonged period. Furthermore, the capacity of the solid solution, in other words the ability to form stable solid solutions with the highest possible active ingredient contents, is also of importance.

The use of so-called "solid dispersions" for improving the solubility and bioavailability of drugs, and the preparation thereof by means of dissolving processes or melt extrusion is generally known, thus for example from "Ch. Leuner, J. Dressman, European Journal of Pharmaceutics and Biopharmaceutics 50 (2000) 47-60". The use of cationic aminoacrylates such as Eudragit® E is also described in general terms in this literature reference.

However, it has been found that Eudragit® E, which is also marketed as Eudragit® E PO, still leaves something to be desired in terms of the stability of the solid dispersion and the loading capacity with active ingredient. Often, at higher active ingredient loadings, active ingredient crystals or relatively large active ingredient domains are produced.

However, the highest possible loading capacity is of great importance.

SUMMARY

Embodiments of a first aspect of the invention are directed to a solid dispersion of hydrophobic active ingredients and cationic copolymers of N,N-diethylaminoethyl methacrylate and methyl methacrylate in a weight ratio of the monomers of from 35:65 to 55:45. In one or more embodiments, the solid dispersion comprises cationic copolymers of N,N-diethylaminoethyl methacrylate and methyl methacrylate in a weight ratio of the monomers of 45:55.

According to one or more embodiments, the solid dispersion comprises 10 to 50% by weight of a hydrophobic active ingredient. In other embodiments, the solid dispersion comprises 20 to 50% by weight of a hydrophobic active ingredient.

In one or more embodiments, the solid dispersion further comprises pharmaceutical additives. In other embodiments, the solid dispersion further comprises plasticizers. In one or more embodiments, the solid dispersion further comprises antioxidants.

Embodiments of a second aspect of the present invention are directed to a process for preparing solid dispersions of hydrophobic active ingredients and cationic copolymers of N,N-diethylaminoethyl methacrylate and methyl methacrylate in a weight ratio of the monomers of from 35:65 to 55:45. In one or more embodiments, a liquid mixture comprising hydrophobic active ingredients and cationic copolymer is prepared and the liquid mixture is converted to the solid form.

In one or more embodiments, the liquid mixture in the process is present in the form of a solution or a melt. In one or more embodiments, the conversion of the liquid mixture to the solid form is undertaken by spray-drying. In other embodiments, the liquid mixture is prepared in a screw extruder with heating and, after extrusion, is solidified by cooling.

According to one or more embodiments, the conversion to the solid form is undertaken by molding the liquid mixture to give a film and solidifying this. In one or more embodiments, the cationic copolymer is used in partially neutralized form. In specific embodiments, the cationic copolymer used is partially neutralized to 2 to 15 mol %, based on the cationic groups. In very specific embodiments, the cationic copolymer used is partially neutralized with a $C_3$-$C_{10}$-dicarboxylic acid.

Embodiments of a third aspect of the present invention are directed to a method of preparing pharmaceutical dosage forms. The method comprises using the solid dispersions according to one or more embodiments as pharmaceutical, cosmetic, agrochemical preparations, dietetic preparations, or as preparations of food supplements.

DETAILED DESCRIPTION

Accordingly, solid dispersions of hydrophobic active ingredients and a cationic copolymer of N,N-diethylaminoethyl methacrylate and methyl methacrylate in a weight ratio of the monomers of from 35:65 to 55:45 have been found.

Furthermore, a process for preparing active-ingredient-containing solid dispersions of hydrophobic active ingredients, comprising, as matrix polymers, cationic copolymers, obtained by free-radical polymerization, of N,N-diethylaminoethyl methacrylate and methyl methacrylate in the weight ratio of the monomers of from 35:65 to 55:45, wherein a liquid mixture of the matrix polymer and at least one hydrophobic active ingredient is converted to a solid, has been found.

The liquid mixture can be present as a solution or melt. The liquid mixture is a homogeneous mixture.

According to one or more embodiments, the matrix polymers are copolymers of N,N-diethylaminoethyl methacrylate and methyl methacrylate in the weight ratio of the monomers of 45:55.

The cationic matrix polymers can be obtained by free-radical emulsion polymerization. As regards the preparation of the matrix polymers based on N,N-diethylaminoethyl methacrylate by emulsion polymerization, reference is made expressly to the disclosure of WO 2009/016258.

In specific embodiments, the copolymer used as matrix polymer is commercially available in the form of an aqueous dispersion as Kollicoat® Smartseal 30 D, BASF SE. The average molecular weight (weight-average) is in the region of 200 000 daltons. The molecular weight can be determined by light scattering.

The cationic matrix polymers can also be used in partially neutralized form. For this, 0.1 to 30, preferably 2 to 20 mol %, of the basic groups can be partially neutralized with suitable acids. For this, all physiologically well tolerated inorganic or organic acids are suitable.

Suitable inorganic acids are hydrochloric acid, sulfuric acid, or phosphoric acid. Also of suitability are monocarboxylic acids such as acetic acid, formic acid, propionic acid, methanesulfonic acid, ethanesulfonic acid, benzoic acid, salicylic acid, gentisic acid, glycolic acid, lactic acid, caproic acid, caprylic acid, capric acid, ascorbic acid, isoascorbic acid, nicotinic acid, 2-hydroxyethanesulfonic acid, dichloroacetic acid, pyroglutamic acid, cinnamic acid, benzenesulfonic acid, p-toluenesulfonic acid, camphorsulfonic acid, gluconic acid, glucuronic acid, hippuric acid, lactobionic acid, mandelic acid, naphthalenesulfonic acid, oleic acid, orotic acid, or tricarboxylic acids such as citric acid.

Of particular suitability are dicarboxylic acids with a chain length of from 3 to 10 carbon atoms. Suitable dicarboxylic acids are primarily unbranched dicarboxylic acids which have terminal acid groups. Suitable dicarboxylic acids are also those which are substituted with one or two hydroxy groups.

According to one or more embodiments of the invention, preference is given to using dicarboxylic acids which have a first $pK_a$ value of greater than 2 and a second $pK_a$ value of greater than 4 for the partial neutralization. In specific embodiments, particular preference is given to using dicarboxylic acids which have a first $pK_a$ value of greater than 2.5 and a second $pK_a$ value of greater than 5. The $pK_a$ value is the negative $\log_{10}$ of the acid constant.

Suitable dicarboxylic acids which carry no further substituents besides the acid groups are the saturated alkanedicarboxylic acids malonic acid, succinic acid, glutaric acid, adipic acid, or sebacic acid. Suitable alkanedicarboxylic acids substituted with one or two hydroxy groups are malic acid (2-hydroxysuccinic acid) or tartaric acid (2,3-dihydroxysuccinic acid). A suitable unsaturated dicarboxylic acid is in particular fumaric acid.

It is also possible to use mixtures of such dicarboxylic acids.

For example, it can be advisable to mix dicarboxylic acids which produce a particularly good resistance of the coatings with those acids which produce a particularly good redispersibility of the powders. Suitable mixtures are e.g. adipic acid with sulfuric acid or succinic acid with oxalic acid.

Within the context of the invention, partial neutralization means that 2 to 25, preferably 4 to 16 mol % of the diethylaminoethyl groups are present in salt form.

In specific embodiments, particular preference is given to using dicarboxylic acids such as adipic acid or succinic acid.

According to the invention, the term "hydrophobic active ingredient" means that an active ingredient has a solubility in water at 20° C. of less than 0.25% (m/m), preferably less than 0.1%, particularly preferably less than 0.01%.

The solid dispersions obtained by the process according to the invention are present in amorphous form. "Amorphous" means that the crystalline fractions of hydrophobic substance are less than 5% by weight, based on the total weight of the solid dispersion.

The solid dispersions obtained according to the invention can be investigated with the help of XRD (X-ray diffraction) and DSC (differential scanning calorimetry) as to amorphicity or the absence of crystallinity. Such an amorphous state can also be referred to as X-ray amorphous state. In one or more embodiments, the assessment is made using XRD.

Using DSC, it can likewise be investigated whether crystalline fractions are present. Crystalline fractions can be identified from sharp melting points. The DSC investigations preferably take place at a heating rate of 20 K/min.

For the purpose of a screening, the assessment of the crystalline fractions can also take place by light microscopy. Suitable light microscopes for this purpose have a resolution of 167 linear pairs/mm, which corresponds to a smallest resolvable object structure of 3 μm.

According to the invention, the solid obtained can be present in solid form as a film or granules or powder, depending on the embodiment.

Of suitability in principle for preparing the solid dispersions are the processes of the film method, spray-drying and melt extrusion, where the solid dispersions are converted to the solid form by converting a liquid mixture in the form of a solution or melt, comprising a hydrophobic acid ingredient and the matrix polymer.

According to one embodiment, all of the ingredients of the preparations are firstly dissolved with one another in a suitable solvent and the solvent is then removed. This can take place by means of all possible types of drying processes, e.g. by spray-drying, film method (evaporation of the solvent), fluidized-bed drying, drying with the application of supercritical gases, freeze-drying. The solution can also be processed to give thin films.

According to a further embodiment, the solid preparations are prepared by extrusion. The polymers can be supplied to the extruder either in pulverulent form or in the form of solutions or dispersions. The dispersions or solutions of the polymer can be converted to a solid form by removing the dispersant or solvent in the extruder in the melt-liquid state and cooling the melt.

Said processes are described in more detail below:

The film method is a process in which a clear solution of the polymer and of the active ingredient is molded to give a thin film which solidifies as a result of the solvent evaporating. Clear solution means that no clouding is evident upon normal inspection. This method is suitable in particular as a screening method in order to determine the loading limits of the solid dispersions in a simple manner. For the screening process, the film can be produced by pouring the solution with the corresponding concentrations of polymer and active ingredient onto glass plates and drawing it out with the help of a blade to give the film. Usually, the films are drawn to layer thicknesses of from 50 to 200 µm. The resulting films are then dried by drawing off the solvent, and solidified as a result. In one or more embodiments, the solvent is removed in vacuo, for example at 1 hPa to 100 hPa. The drying can take place, for example, in a vacuum drying cabinet or in comparable vacuum devices. Additionally, the removal of the solvent can be effected by the action of temperature.

For the screening process, the films produced are then stored under controlled climatic conditions for defined periods of time—generally 14 days. The climatic conditions are 23° C./53% relative humidity.

The films can then be evaluated by microscope at 40 times magnification. Clear films are a sign of amorphous systems. Cloudy films point to relatively large crystalline fractions.

In principle, films can also be prepared for use in commercial drug forms. In this connection, the solution of polymer and active ingredient is likewise poured onto suitable surfaces using appropriate pouring devices and drawn out to the desired layer thickness or applied to rollers and dried.

Suitable solvents are in principle all solvents which dissolve the polymers and the hydrophobic active ingredients equally well.

According to a further embodiment of the invention, spray-drying is suitable for preparing the solid dispersions. To prepare the polymer/active ingredient mixture, the substances are weighed into a suitable container. The corresponding amount of solvent is added and the mixture is stirred until the polymer and the active ingredient have completely dissolved.

Suitable solvents are, for example, acetone, dichloromethane, ethanol, propanol, methanol, isopropanol, dimethylformamide, ethyl acetate, methyl ethyl ketone, tetrahydrofuran, dioxane, diethyl ether.

The liquid to be dried can then be converted to a solid by means of atomization with removal of the solvent. In principle, an atomization can take place via nozzles or via rotating disks. Suitable nozzles are single-material or multi-material nozzles such as, for example, two-material nozzles. A heated inert gas flowing concurrently dries the dispersed drops to give solid particles with particle diameters in the range from 5-100 µm. The drying gas used in one or more embodiments is nitrogen. In the entry region of the spray drier, the drying gas is preferably supplied tangentially. The dry product particles can be separated off in a cyclone or a filter. The temperature of the drying gas can be 30 to 150° C. The atomizing pressure can be 0.1 to 20 MPa. The spray drying can also be arranged in the form of an agglomerating spray-drying (e.g. FSD technology), which leads to larger agglomerates of 100-1000 µm.

According to a further embodiment of the invention, the solid dispersions are prepared by means of a screw extruder. Of suitability in principle for the extrusion process are the customary extruder types. Preference is given to using twin-screw extruders. However, multi-shaft extruders having more than two screws are also suitable. The extruders suitable for this purpose usually comprise a housing, a drive unit with transmission, and a processing unit which consists of the extruder shaft or shafts equipped with the screw elements, modular construction being presumed in this case. Customary screw elements are conveying elements, kneading disks, backup elements or elements with specific geometries which influence the influencing of specific parameters. Such elements are known to the person skilled in the art, who is able to establish suitable screw geometries by means of a few preliminary experiments. In this connection, it has to be ensured that the shear load does not become too high.

Usually, it is also advisable to establish a relatively large free volume in the intake zone, and then to reduce the increase in due course.

The individual zones of the extruder are usually heatable or coolable. The temperature adjustment is governed by the glass transition temperature of the mixture of cationic polymer, hydrophobic active ingredient and further possible admixtures to be extruded. The temperature can be adjusted by regulating the internal temperature of the cylinder. What temperature is specifically established is governed by the decomposition temperature of the components and by the melting point of the active ingredient.

To prepare the liquid mixture, the mixture of the components hydrophobic active ingredient and matrix polymer and optionally further auxiliaries is heated to temperatures above the glass transition temperature of the mixture. The glass transition temperature of the mixture can be ascertained by means of DSC at a heating rate of 20 K/min.

The temperature of the individual extruder zones can vary between 30 and 200° C., preferably 40 to 180° C., the internal cylinder temperatures being intended here. In the first zone, the temperature is chosen to be low and increases in the subsequent zones until it is sufficiently far above the glass transition temperature of the mixture for a homogeneous melt to form. Homogeneous melts have a clear appearance.

Which temperature profile is selected in specific cases is governed by the composition of the formulation.

The formulations for extrusion can be supplied to the extrusion process in different ways. The following methods A-E can be used in principle:

| | |
|---|---|
| A | physical powder mixing of matrix polymer and active ingredient and supply of this powder mixture to the extruder and then common melting or dispersion of the active ingredient in the polymer melt |
| B | supply of the active ingredient via a separate bypass into unmolten polymer mixture and subsequent common melting or dispersion of the unmolten active ingredient in the polymer melt |
| C | supply of the active ingredient via a side feed into molten matrix polymer |
| D | matrix polymer solution with active ingredient dispersed or dissolved therein in partly degassed polymer melt or unmolten polymer mixture; |
| E | process according to A-D, where additionally solvent is introduced into the extruder and evaporated again |

If solvent is additionally added, the solvents specified in connection with the preparation of films can be used.

The liquid mixture produced in the extruder in the form of a melt of matrix polymer, hydrophobic active ingredient and optionally further auxiliaries can be extruded via one or more nozzles.

The round nozzles used can have a diameter of from 0.5 to 5 mm. Other nozzle shapes, such as slot nozzles, can likewise be used, especially if a relatively large material throughput is desired.

The resulting solidified extrudate strands can be processed with a granulator to give granules which can in turn be comminuted (ground) further to give a powder. The granules or powder can be filled into capsules or pressed to give tablets using customary tableting auxiliaries. In this connection, it is also possible to use further release-controlling auxiliaries.

In addition, it is possible to use water, organic solvents, buffer substances or plasticizers during the extrusion. In particular, water or volatile alcohols are options here. This process enables reaction at relatively low temperature. The amounts of solvent or plasticizer are usually between 0 and 30% by weight of the extrudable mass. The water or solvent can already be removed by a venting point in the extruder at standard pressure or by applying a vacuum. Alternatively, these components evaporate when the extrudate leaves the extruder and the pressure is reduced to standard pressure. In the case of less volatile components, the extrudate can correspondingly be dried subsequently.

According to one or more embodiments, at the time of extruding the melt through the nozzles, the melts are free from solvents. This means that the solvent fraction is less than 1% by weight.

In one particular variant of the preparation process, the extrusion is directly followed by calendering the thermoplastic mass to give a tablet-like compact, which constitutes the ultimate administration form. In this variant, it may be advisable to add further constituents, such as e.g. polymers to adjust the glass transition temperature and the melt viscosity, disintegrants, solubilizers, plasticizers, dyes, flavorings, sweeteners, etc. already before or during the extrusion. In principle, these substances can also be used when the extrudate is first comminuted and then pressed to give tablets.

The amorphous solid dispersions obtained according to the invention can have a loading of hydrophobic active ingredient of from 2 to 60% by weight, based on the total weight of the solid dispersion. In one or more embodiments, the content of hydrophobic active ingredient is 10 to 50% by weight, preferably 20 to 50% by weight. The content of cationic matrix polymer of diethylaminoethyl methacrylate and methyl methacrylate can be 5 to 95% by weight. Additionally, the dispersions can comprise further pharmaceutical additives. The amount of other additives can be 0.1 to 60% by weight, based on the total preparation. As a result of adding (up to 50% by weight of the polymer matrix) of hydrophilic polymers, it is possible to influence the disintegration rate of the resulting extrudates during the release. By increasing the hydrophilicity, a more rapid wetting and a more rapid disintegration in the release can be achieved. For this purpose, hydrophilic polymers with low molecular weights (<100 000 daltons) are particularly suitable. Hydrophilic polymers with a higher molecular weight (>100 000 daltons) can be regarded as a stabilizer for the resulting solid solution since they increase the rigidity of the matrix and prevent the crystallization of the active ingredient from supersaturated solutions. Consequently, stable supersaturated solid solutions can be prepared which have a particularly high fraction of drug.

The hydrophilic polymers are generally water-soluble, at least in a certain pH range. In this connection, water-soluble means that at least 0.1 g dissolve in 1 ml at 20° C.

Suitable hydrophilic polymers are for example: polyvinylpyrrolidones with K values of from 12 to 90, N-vinylpyrrolidone copolymers, for example copolymers with vinyl esters such as vinyl acetate or vinyl propionate, in particular copolymers of N-vinylpyrrolidone and vinyl acetate in the weight ratio 60:40, polyvinyl alcohols, hydroxyalkylated cellulose derivatives such as hydroxypropylcellulose (HPC) or hydroxypropylmethylcellulose (HPMC), hydroxyalkylated and carboxyalkylated cellulose derivatives, acrylic acid-methacrylic acid copolymers.

Polyethylene glycols with average molecular weights of from 1000 to 6000 are also suitable. Also of suitability are graft polymers of polyethylene glycol and polyvinyl alcohol units, as are commercially available as Kollicoat® IR, BASF, or mixtures of such graft polymers with polyvinyl alcohol. Also of suitability are graft copolymers of polyethylene glycol and N-vinylcaprolactam and vinyl acetate units grafted thereon, such as the commercially available Soluplus®, BASF SE.

To adjust the glass transition temperature of the formulation, water-soluble polymers with a high glass transition temperature such as e.g. polyvinylpyrrolidone with K values of 17-120, hydroxyalkylcelluloses or hydroxalkyl starches can be used. An excessively high glass transition temperature of the formulation can be lowered by adding plasticizers. Of suitability in principle for this purpose are all plasticizers which are also used for pharmaceutical coatings, such as e.g. triethyl citrate, tributyl citrate, acetyltributyl citrate, triacetin, propylene glycol, polyethylene glycol 400, dibutyl sebacate, glycerol monostearate, lauric acid, cetylstearyl alcohol. Such plasticizers can be used in amounts of from 0.1 to 20% by weight, based on the total weight of the dispersion.

Furthermore, surfactants, which reduce the melt viscosity and thus the extrusion temperature, can additionally also be incorporated into the preparations. These substances can also have a positive influence on the possible crystallization, and also bring about better wetting of the formulation and more rapid dissolution. Suitable substances are ionic and nonionic surfactants, such as, for example, Kolliphor™ HS 15 (Macrogol 15 Hydroxystearate), Tween® 80, polyoxyethylated fatty acid derivatives such as Kolliphor™ RH 40 (polyoxyl 40 Hydrogenated Castor Oil, USP), Kolliphor™ EL (Polyoxyl 35 Castor Oil, USP), poloxamers, docusate sodium or sodium lauryl sulfate.

Furthermore, it may be advisable to add antioxidants to the solid dispersions in amounts of 0.1 to 10% by weight, based on the total weight of the solid dispersion. According to the invention, suitable antioxidants are sparingly water-soluble antioxidants, i.e. antioxidants whose solubility in water at 20° C. is not more than 1 g/l.

Of suitability here as antioxidants are primarily the lipophilic substances tocopherol, tocopherol acetate, ascorbyl palmitate, ascorbyl stearate, t-butylhydroquinone, t-butylhydroxyanisole, t-butylhydroxytoluene, octyl gallate, or dodecyl gallate or combinations thereof.

The preparations obtained by these processes can be used in principle in all areas in which water-insoluble or sparingly water-soluble substances are either to be used in aqueous preparations or are to develop their effect in an aqueous medium.

Within the context of the present invention, hydrophobic active ingredients are understood as meaning biologically active substances such as pharmaceutical active ingredients for humans and animals, cosmetic or agrochemical active ingredients, or food supplements or dietetic active ingredients.

Furthermore, suitable solubilizing hydrophobic active ingredients are also dyes such as inorganic or organic pigments.

According to the invention, suitable biologically active substances are in principle all solid active ingredients which have a melting point which is below the decomposition point under extrusion conditions of the copolymers. The copolymers can generally be extruded at temperatures up to 200° C. The lower temperature limit is governed by the composition of the mixtures to be extruded and the sparingly soluble substances to be processed in each case.

The active ingredients can come from any indication area.

Examples which may be mentioned here are benzodiazepines, antihypertensives, vitamins, cytostatics—in particular taxol, anesthetics, neuroleptics, antidepressants, antivirals, such as, for example, anti-HIV drugs, antibiotics, antimycotics, antidementia agents, fungicides, chemotherapeutics, urologics, thrombocyte aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, narcotics, lipid-lowering drugs, liver therapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, blood-flow stimulators, diuretics, diagnostics, corticoids, cholinergics, billiary therapeutics, antiasthmatics, broncholytics, beta-receptor blockers, calcium antagonists, ACE inhibitors, arteriosclerosis drugs, antiphlogistics, anticoagulants, antihypertensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists, slimming aids.

Among the aforementioned pharmaceutical preparations, particular preference is given to those which are orally administrable formulations. To produce pharmaceutical administration forms such as, for example, tablets, the extrudates can be admixed with customary pharmaceutical auxiliaries.

These are substances from the class of the fillers, plasticizers, solubility promoters, binders, silicates, and also disintegrants and absorbents, lubricants, flow agents, dyes, stabilizers such as antioxidants, wetting agents, preservatives, mold release agents, aromas or sweeteners, preferably fillers, plasticizers and solubility promoters.

Fillers which can be added are e.g. inorganic fillers such as oxides of magnesium, aluminum, silicon, titanium carbonate or calcium carbonate, calcium phosphates or magnesium phosphates or organic fillers such as lactose, sucrose, sorbitol, mannitol.

Suitable plasticizers are, for example, triacetin, triethyl citrate, glycerol monostearate, low molecular weight polyethylene glycols or poloxamers.

Suitable additional solubility promoters are interface-active substances with an HLB (HydrophilicLipophilicBalance) value greater than 11, for example hydrogenated castor oil ethoxylated with 40 ethylene oxide units (Kolliphor™ RH 40), castor oil ethoxylated with 35 ethylene oxide units (Kolliphor™ EL), polysorbate 80, poloxamers or sodium lauryl sulfate.

Lubricants which can be used are stearates of aluminum, calcium, magnesium and tin, and also magnesium silicate, silicones and the like.

Flow agents which can be used are, for example, talc or colloidal silicon dioxide.

A suitable binder is, for example, microcrystalline cellulose.

Disintegrants may be crosslinked polyvinylpyrrolidone or crosslinked sodium carboxymethyl starch. Stabilizers can be ascorbic acid or tocopherol.

Dyes are e.g. iron oxides, titanium dioxide, triphenylmethane dyes, azo dyes, quinoline dyes, indigotin dyes, carotinoids, in order to color the administration forms, opacifiers such as titanium dioxide or talc, in order to increase the transparency to light and in order to save on dyes.

Besides the application in cosmetics and pharmacy, the preparations prepared according to the invention are also suitable for use in the food sector, for example for the incorporation of sparingly water-soluble or water-insoluble nutrients, auxiliaries or additives, such as e.g. fat-soluble vitamins or carotinoids. Examples which may be mentioned are beverages colored with carotinoids.

The use of the preparations obtained according to the invention in agrochemistry can comprise inter alia formulations which comprise pesticides, herbicides, fungicides or insecticides, primarily also those preparations of crop protection compositions which are used as spraying or watering formulations.

With the help of the process according to the invention it is possible to obtain so-called solid solutions with sparingly-soluble substances. According to the invention, solid solutions is the term used to refer to the systems in which no crystalline fractions of the sparingly-soluble substance are observed.

EXAMPLES

According to the invention, the matrix polymer used was a polymer prepared analogously to Example 1 of WO 2009/016258, obtained from methyl methacrylate and diethylaminoethyl methacrylate in the weight ratio of 55:45, which is commercially available as Kollicoat® Smartseal 30D in the form of an aqueous dispersion. Molar ratio of diethylaminoethyl methacrylate:methyl methacrylate 3:7; Tg: in the region of 63° C. (measured by means of DSC at a heating rate of 20° K/min); weight average (determined by SEC light scattering in the region of 200 000 daltons).

The polymer was used either as a freeze-dried powder or as a spray-dried powder.

In some examples, the polymer was also used in partially neutralized form:
degree of partial neutralization 6 mol: 6 mol % of the basic groups partially neutralized with adipic acid
degree of partial neutralization 8 mol: 8 mol % of the basic groups partially neutralized with succinic acid.

Eudragit® EPO, used for comparison, is a basic copolymer of dimethylaminoethyl acrylate, butyl acrylate and methyl methacrylate in the molar ratio 2:1:1.

Process 1: Film Method
General Procedure

To prepare the polymer/active ingredient mixture, the substances were weighed in the respective amounts into a 50 ml penicillin bottle.

| Concentration [% by wt.] | Polymer [g] | Active ingredient [g] | Solvent [g] |
|---|---|---|---|
| Blank | 2.00 | — | 18.00 |
| 5 | 2.00 | 0.11 | 17.89 |
| 10 | 2.00 | 0.22 | 17.78 |
| 15 | 2.00 | 0.35 | 17.65 |
| 20 | 2.00 | 0.50 | 17.50 |
| 25 | 2.00 | 0.67 | 17.33 |
| 30 | 2.00 | 0.86 | 17.14 |
| 35 | 2.00 | 1.08 | 16.92 |
| 40 | 2.00 | 1.34 | 16.66 |
| 45 | 2.00 | 1.63 | 16.37 |
| 50 | 2.00 | 2.00 | 16.00 |

All of the mixtures were stirred for 24 h on a magnetic stirrer until the constituents had dissolved. After visually assessing the solution (clear solution), the solvent was drawn out on a glass plate using a 120 μm blade. The resulting film was dried for 0.5 h at room temperature of 22+/−2° C. in a fume cupboard and then for 0.5 h in a vacuum drying cabinet at 50° C. and 1 MPa. The loading limit of the active ingredient in the polymer was assessed visually after storage for 7 days at 23° C./54% relative humidity by means of microscopic analysis. Clear films (without active ingredient crystals) indicate molecularly disperse solutions and cloudy films (with active ingredient crystals) indicate crystalline systems.

Process 2: Spray-Drying

General Procedure

To prepare the polymer/active ingredient mixture, the substances were weighed into an appropriate storage vessel. The corresponding amount of solvent was added and the mixture was stirred until the polymer and the active ingredient had completely dissolved. For the fenofibrate formulations, the solvent was acetone, for the itraconazole formulations the solvent was dichloromethane and for the formulations with naproxen, acetone was used as solvent. The solids fraction of the spraying solution was 20% by weight for all experiments. The spray-drying was carried out on a laboratory scale.

The liquid to be dried was atomized using a two-material nozzle. A heated gas (here nitrogen) flowing concurrently dries the distributed drops to give solid particles with particle diameters in the range 5-20 μm. In the entry area of the spray drier, the drying gas is supplied tangentially. The dry product particles are separated off in a cyclone.

Process 3: Extrusion

General Procedure

The twin-screw extruder which was used for preparing the formulations described in the examples below had a screw diameter of 16 mm and a length of 40D. The extruder consisted of 10 heatable zones including nozzle. The screw configuration was selected such that in zones 5 and 7 kneading elements were used, otherwise conveying elements. The nozzle (zone 10) was likewise heated.

For the extrusion examples listed later, the process parameters used are described. The stated zone temperatures are the internal temperature of the cylinder.

Characterization of the Resulting Products

Characterization of the Solid Dispersions was Carried Out with Visual Assessment, XRD (X-Ray Diffraction) and DSC (Differential Scanning Calorimetry).

Upon visual assessment of the stable solid solutions, no amorphous constituents are apparent. The visual assessment can take place with a light microscope either with or without polarization filter at 40 times magnification.

The solid solutions prepared from the extrusion process and from the spray drying were investigated by means of XRD or DSC as to crystallinity and/or amorphicity using the following equipment and conditions:

XRD

Instrument: D 8 Advance diffractometer with 9-fold sample changer (Bruker/AXS)

Measurement method: θ–θ geometry in reflection 2 theta angle range: 2-40°

Step width: 0.02°

Measurement time per angle step: 2.4 s

Divergence slit: Göbel mirror with 1.0 mm inserted aperture

Antiscattering slit: Soller slit

Detector: Sol-X detector

Temperature: room temperature

Generator setting: 40 kV/50 mA

DSC

Instrument: Q2000 (TA Instruments, USA)

Drying: drying of the samples overnight at 40° C. in vacuo and subsequent weighing into a crucible pressure-tight to 20 bar Heating rate: 20 K/min Characterization of Solid Solutions by Means of Active Ingredient Release The prepared solid solutions from the extrusion process and the spray-drying were investigated by means of manual or semi-automatic active ingredient release:

Manual Active Ingredient Release from the Itraconazole Extrudates (Method 1)

The active ingredient release was carried out according to USP apparatus (paddle method) 2, 700 ml 0.08 N HCl, 37° C., 50 rpm (BTWS 600, Pharmatest). The extrudate strands were reduced in size to a length of 3 mm using a granulator and fed to the release in this form. In each case, 100 mg of active ingredient (non-sink conditions) were used per release vessel. The released active ingredient was detected manually after stipulated time points and after filtration through a 10 μm filter by UV-VIS spectroscopy (Agilent 8453 UV-VIS spectrometer, Agilent).

Active Ingredient Release from the Itraconazole Extrudates (Method 2)

The active ingredient release was carried out according to USP apparatus (paddle method) 2, 700 ml 0.08 N HCl, 37° C., 75 rpm (BTWS 600, Pharmatest). The extrudate strands were reduced in size to a length of 3 mm using a granulator and fed to the release in this form. In each case, 100 mg of active ingredient (non-sink conditions) were used per release vessel. The released active ingredient was detected semi-automatically after stipulated time points and after filtration through a 45 μm filter by UV-VIS spectroscopy (Agilent 8453 UV-VIS spectrometer, Agilent).

Active Ingredient Release from the Danazol Extrudates (Method 3)

The active ingredient release was carried out according to USP apparatus (paddle method) 2, 700 ml 0.08 N HCl with 0.1% Tween® 80, 37° C., 100 rpm (BTWS 600, Pharmatest). The extrudate strands were reduced in size to a length of 3 mm using a granulator. The reduced extrudate strands were comminuted using a MF 10 basic mill (sieve: 0.5 mm, IKA Werke) and fed in this form to the release. In each case, 100 mg of active ingredient (non-sink conditions) were used per release vessel. The released active ingredient was detected semi-automatically after stipulated time points and after filtration through a 45 μm filter by UV-VIS spectroscopy (Agilent 8453 UV-VIS spectrometer, Agilent).

Active Ingredient Release from the Products of Spray-Drying (Method 4)

The active ingredient release was carried out according to USP apparatus (paddle method) 2, 700 ml 0.08 N HCl, 37° C., 75 rpm (BTWS 600, Pharmatest). The products by means of spray-drying were poured into gelatin capsules (size: 0) and supplied to the release in this form. In order to prevent the capsules from floating, they were weighed down using a platinum wire. In each case, 100 mg of active ingredient (non-sink conditions) were used per release vessel. The released active ingredient was detected semi-automatically after stipulated time points and after filtration through a 45 μm filter by UV-VIS spectroscopy (Agilent 8453 UV-VIS spectrometer, Agilent).

Example 1

Loading capacity of Kollicoat® Smartseal and partially neutralized Kollicoat® Smartseal with different active ingredients compared to Eudragit® EPO. The concentrations given here in the films refer to the loading capacity of the molecularly disperse dissolved active ingredient, i.e. there are still no crystals of the active ingredient observed in the film. Higher loadings lead to crystalline fractions.

| Active ingredients in % | Films with Eudragit® EPO | Films with Kollicoat® Smartseal freeze-dried | Films with Kollicoat® Smartseal + 6 mol partially neutralized | Films with Kollicoat® Smartseal + 8 mol partially neutralized | Solvent |
|---|---|---|---|---|---|
| Itraconazole | 30 | 50 | 35 | 35 | Cl$_2$CH$_2$ |
| Fenofibrate | 20 | 50 | 20 | 20 | DMF |
| Carbamazepine | <10 | 20 | 30 | 30 | DMF |
| Estradiol | <10 | 50 | 50 | 30 | DMF |
| Clotrimazole | 20 | 35 | 35 | 35 | DMF |
| Danazol | <10 | 50 | 50 | 50 | DMF |
| Cinnarizine | <10 | 20 | 20 | 20 | DMF |
| Ibuprofen 50 | <10 | 30 | 30 | 30 | DMF |
| Loperamide HCL | <10 | 50 | 50 | 50 | DMF |
| Naproxen | 30 | 50 | 50 | 50 | DMF |

DMF dimethylformamide
Cl$_2$CH$_2$ dichloromethane
Kollicoat® Smartseal and Kollicoat® Smartseal (partially neutralized) dissolve active ingredients as solid solution significantly better than Eudragit® EPO.

Example 2

2925 g of Kollicoat® Smartseal (freeze-dried) and 75 g of butylhydroxytoluene were weighed into a Turbula mixing container and mixed for 10 minutes in the Turbula mixer T10B. This mixture was dosed into the extruder using the gravimetric dosing unit DDW-MD2-DDSR20-10 (Brabender Technologie) and the active ingredient fenofibrate using the gravimetric dosing unit Mini Twin MT1 (Brabender Technolgie).

The mixture was extruded under the following conditions using the twin-screw extruder with a screw diameter of 16 mm and a length of 40D:
zone temperature 1st cylinder: 45° C.; 2nd cylinder: 85° C.
zone temperature from the 3rd cylinder: 150° C.
screw speed 50 rpm
throughput: 500 g/h
nozzle diameter 3 mm The preparation with a mass fraction of 34% (w/w) fenofibrate were investigated by XRD and found to be amorphous.

Example 3

2925 g of Kollicoat® Smartseal (freeze-dried) and 75 g of butylhydroxytoluene were weighed into a Turbula mixing container and mixed for 10 minutes in the Turbula mixer T100B. This mixture was dosed into the extruder using the gravimetric dosing unit DDW-MD2-DDSR20-10 (Brabender Technologie). 250 g of the Kollicoat® Smartseal mixture (Kollicoat® Smartseal with butylhydroxytoluene) and 250 g of itraconazole were weighed into a Turbula mixing container and mixed for 10 minutes in the Turbula mixer T2C. This active ingredient mixture was dosed into the extruder via a second gravimetric dosing system Mini Twin MT1 (Brabender Technologie).

The mixture was extruded under the following conditions using the twin-screw extruder with a screw diameter of 16 mm and a length of 40D:
zone temperature 1st cylinder: 50° C.; 2nd cylinder: 100° C.
zone temperature from the 3rd cylinder to cylinder 10: 160° C.
screw speed 50 rpm
throughput: 400 g/h
nozzle diameter 3 mm The solid solutions were investigated with XRD and up to 38% itraconazole found to be amorphous. The release (method 1) of the active ingredient from an extrudate in 0.08 N HCl after 2 h was 89% (FIG. 1).

Figure 1:
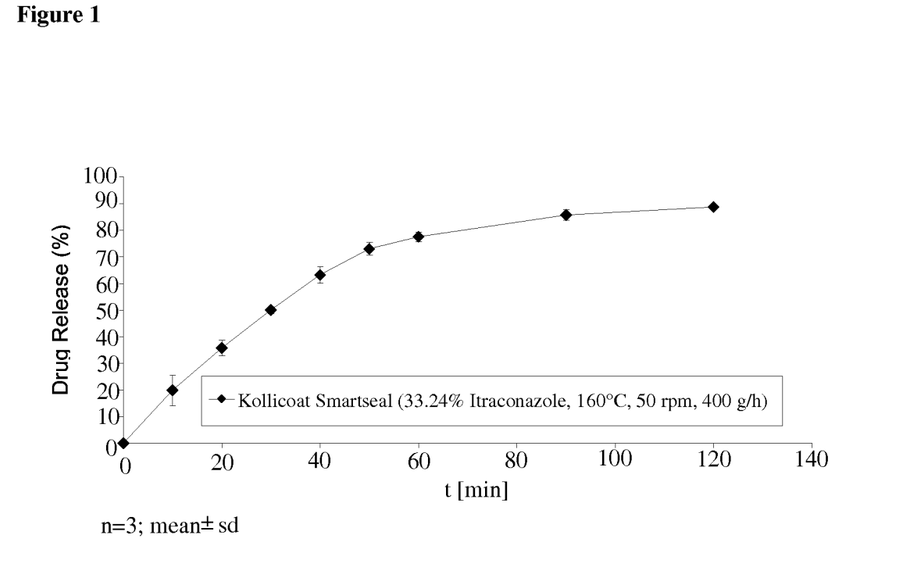
FIG. 1 is a graph showing the release of active ingredient itraconazole from the Kollicoat® Smartseal extrudate.

FIG. 1: Active ingredient release of itraconazole from the Kollicoat® Smartseal extrudate in 0.08 N HCl at 50 rpm Example 4

The corresponding amount of the respective polymer (Kollicoat® Smartseal, Kollicoat® Smartseal 8 mol partially neutralized, Eudragit® EPO) and the corresponding active ingredient carbamazepine were weighed into a Turbula mixing container (total amount of polymer+active ingredient was in each case 400 g) and mixed for 10 minutes in the Turbula mixer T2C. This mixture was dosed into the extruder using the gravimetric dosing unit DDW-MD2-DDSR20-10 (Brabender Technologie).

The mixture was extruded under the following conditions using the twin-screw extruder with a screw diameter of 16 mm and a length of 40D:
zone temperature 1st cylinder: 40° C.; 2nd cylinder: 80° C.
zone temperature from the 3rd cylinder to cylinder 10: 160° C.
screw speed 200 rpm
throughput: 1000 g/h
nozzle diameter 3 mm The prepared preparations were analyzed using DSC for amorphous and crystalline active ingredients in the formulation.

| Polymer | Carbamazepine (% w/w) | | | | | | | | |
|---|---|---|---|---|---|---|---|---|---|
| | 10 | 15 | 20 | 25 | 30 | 35 | 40 | 45 | 50 |
| Kollicoat® Smartseal | | A | A | A | K | | | | |
| Kollicoat® Smartseal 8 mol partially neutralized | | | A | K | K | K | | | |
| Eudragit® EPO | A | K | K | K | | | | | |

A amorphous formulation (without active ingredient crystals)
K crystalline formulation (with active ingredient crystals)

Comparison of the results of the solid solution (amorphous formulations) with carbamazepine from the extrusion compared to the film method.

| Polymer | Loading film method [%] | Loading extrusion [DSC, %] |
|---|---|---|
| Kollicoat® Smartseal | 20 | 25 |
| Kollicoat® Smartseal 8 mol partially neutralized | 30 | 20 |
| Eudragit® EPO | <10 | 10 |

Kollicoat® Smartseal and Kollicoat® Smartseal 8 mol partially neutralized exhibit higher loadings of carbamazepine in the extrusion and in the film method compared to the loadability of Eudragit® EPO.

Example 5

The corresponding amount of the particular polymer (Kollicoat® Smartseal, Kollicoat® Smartseal 6 mol partially neutralized, Eudragit® EPO) and the corresponding active ingredient itraconazole were weighed into a Turbula mixing container (total amount of polymer+active ingredient was in each case 400 g) and mixed for 10 minutes in the Turbula mixer T2C. This mixture was dosed into the extruder using the gravimetric dosing unit DDW-MD2-DDSR20-10 (Brabender Technologie).

The mixture was extruded under the following conditions with the twin-screw extruder with a screw diameter of 16 mm and a length of 40D:

zone temperature 1st cylinder: 50° C.; 2nd cylinder: 90° C.

zone temperature from the 3rd cylinder to cylinder 9: 160° C.

zone temperature 10th cylinder: 150° C.

screw speed 200 rpm throughput: 1000 g/h nozzle diameter 3 mm

The formulations produced were visually assessed and evaluated in terms of amorphous (clear extrudates) and crystalline active ingredients in the formulation (start of clouding).

| | Itraconazole (% w/w) | | | | | | | |
|---|---|---|---|---|---|---|---|---|
| Polymer | 10 | 15 | 20 | 25 | 30 | 35 | 40 | 45 | 50 |
| Kollicoat® Smartseal | | | | | A | A | A | K | K |
| Kollicoat® Smartseal 6 mol partially neutralized | | | | A | A | K | K | K | K |
| Eudragit® EPO | | | A | A | K | K | K | K | K |

A amorphous formulation (without active ingredient crystals)
K crystalline formulation (with active ingredient crystals)

Comparison of the results of the solid solution (amorphous formulations) with itraconazole from the extrusion compared to the film method.

| Polymer | Loading film method [%] | Loading extrusion [DSC, %] |
|---|---|---|
| Kollicoat® Smartseal | 50 | 40 |
| Kollicoat® Smartseal 6 mol partially neutralized | 35 | 30 |
| Eudragit® EPO | 30 | 25 |

Kollicoat® Smartseal and Kollicoat® Smartseal 6 mol partially neutralized exhibit higher loadings of itraconazole in the extrusion and in the film method compared to the loadability of Eudragit® EPO.

The release (method 2) of itraconazole (30+45% w/w) from the extrudates with Kollicoat® Smartseal, 30% (w/w) Kollicoat® Smartseal 6 mol partially neutralized and Eudragit® EPO with 25, 30, 35% (w/w) itraconazole in 0.08 N HCl exhibit a rapid and complete release of the active ingredient after 1.5 h.

| Formulation | Release after 90 min [% w/w] |
|---|---|
| 30% itraconazole in Kollicoat® Smartseal | 99 |
| 45% itraconazole in Kollicoat® Smartseal | 98 |
| 30% itraconazole in Kollicoat® Smartseal 6 mol partially neutralized | 97 |
| 25% itraconazole in Eudragit® EPO | 99 |
| 30% itraconazole in Eudragit® EPO | 98 |
| 35% itraconazole in Eudragit® EPO | 101 |

Example 6

The corresponding amount of the respective polymer (Kollicoat® Smartseal, Eudragit® EPO) and the corresponding active ingredient danazol were weighed into a Turbula mixing container (total amount polymer+active ingredient was in each case 400 g) and mixed for 10 minutes in a Turbula mixer T2C. This mixture was dosed into the extruder using the gravimetric dosing unit DDW-MD2-DDSR20-10 (Brabender Technologie).

The mixture was extruded under the following conditions using the twin-screw extruder with a screw diameter of 16 mm and a length of 40D:

zone temperature 1st cylinder: 40° C.; 2nd cylinder: 80° C.

zone temperature from the 3rd cylinder to cylinder 10: 180° C.

screw speed 200 rpm throughput: 1000 g/h nozzle diameter 3 mm

The preparations were analyzed using XRD for amorphous and crystalline active ingredients in the formulation.

| | Danazol (% w/w) | | | | | | | |
|---|---|---|---|---|---|---|---|---|
| Polymer | 10 | 15 | 20 | 25 | 30 | 35 | 40 | 45 | 50 |
| Kollicoat® Smartseal | | | | A | | | | | |
| Eudragit® EPO | | | | A | | | | | |

A amorphous formulation (without active ingredient crystals)
K crystalline formulation (with active ingredient crystals)

Figure 2:
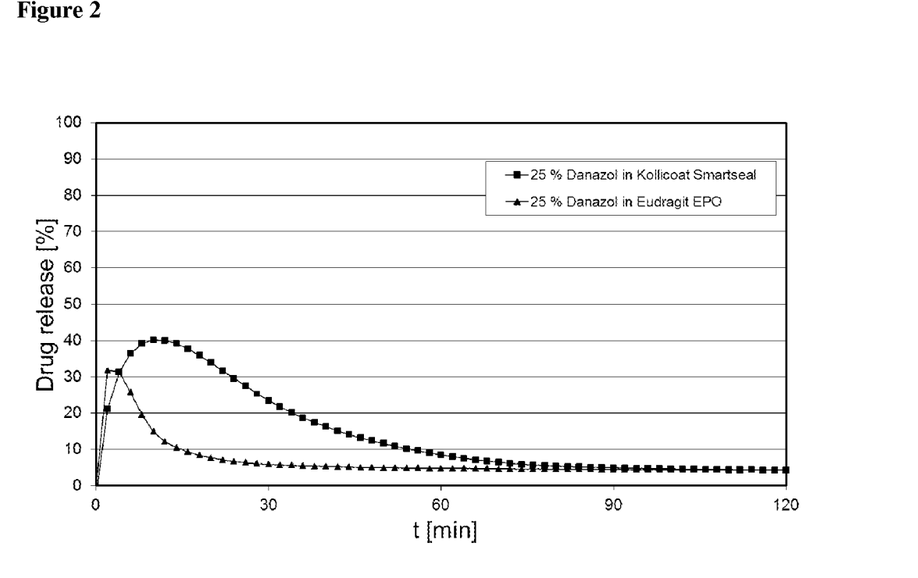
FIG. 2 is a graph showing the release curves of active ingredient danazol from Kollicoat® Smartseal and Eudragit® EPO extrudates.

The release (method 3) of 25% (w/w) danazol from the ground extrudates with Kollicoat® Smartseal and Eudragit® EPO in 0.08 N HCl with 0.1% Tween® 80 is shown in FIG. 2. The recrystallization of danazol starts in the case of the Eudragit® EPO extrudate from 5 minutes, in the case of Kollicoat® Smartseal extrudate from 14 minutes and can thus be extended by 9 minutes. The maximum active ingredient release of danazol can also additionally be increased to 40% in this formulation. It is assumed that a larger area under the release curve of Kollicoat Smartseal also leads to a greater bioavailability.

The release curves are shown in FIG. 2: active ingredient release of danazol from Kollicoat® Smartseal and Eudragit® EPO extrudates (ground) in 0.08 N HCl with 0.1% Tween® 80 at 100 rpm.

Example 7

Loading capacity of Kollicoat® Smartseal with different active ingredients in the spray-drying. Spray-drying experiments carried out on the laboratory scale:
1. Itraconazole: Kollicoat® Smartseal with 40+50% (w/w) itraconazole
2. Fenofibrate: Kollicoat® Smartseal with 40+50% (w/w) fenofibrate
3. Naproxen: Kollicoat® Smartseal with 40+50% (w/w) naproxen Experimental Conditions:

| Process parameter | Itraconazole | Fenofibrate | Naproxen |
|---|---|---|---|
| Nozzle | 1.2 mm | 1.2 mm | 1.2 mm |
| Nozzle pressure | 0.3 MPa abs. | 0.3 MPa abs. | 0.3 MPa abs. |
| Temperature of nozzle gas | room temperature | room temperature | room temperature |
| Temperature of entry air | 50° C. | 50° C. | 50° C. |
| Temperature of exit air | 38° C. | 36° C. | 36° C. |

| Active ingredient | Loading film method [%] | Loading spray-drying [DSC, %] | Loading spray-drying [XRD, %] |
|---|---|---|---|
| Itraconazole | 50 | 50 | 50 |
| Fenofibrate | 50 | 40 | — |
| Naproxen | 50 | 50 | 50 |

Kollicoat ® Smartseal dissolves high concentrations of the active ingredients itraconazole, fenofibrate and naproxen as solid solution in the spray-drying, comparable with the results from the film method.

Figure 3:
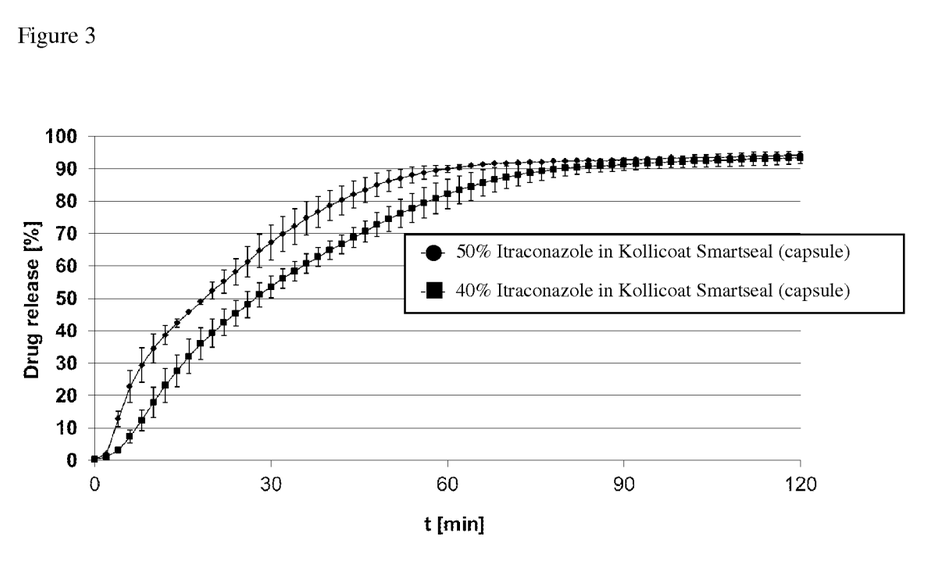
FIG. 3 is a graph showing the release of active ingredient itraconazole from Kollicoat® Smartseal.

The release (method 4) of itraconazole (40+50% w/w) from Kollicoat® Smartseal (spray-drying) in 0.08 N HCl shows a rapid and complete release of the active ingredient after 2 h (FIG. 3).

The active ingredient release of itraconazole is shown in FIG. 3: release of itraconazole from Kollicoat® Smartseal, prepared with the spray-drying method, in 0.08 N HCl at 75 rpm.

What is claimed is:

1. A solid dispersion comprising a hydrophobic active ingredient and an antioxidant embedded in a polymer matrix that comprises a cationic copolymer of N,N-diethylaminoethyl methacrylate and methyl methacrylate in a weight ratio of the monomers of from 35:65 to 55:45, wherein the solid dispersion comprises 10 to 50% by weight of the hydrophobic active ingredient and the hydrophobic active ingredient is not an antioxidant and wherein the hydrophobic active ingredient is present in amorphous form, is embedded in the polymer matrix in microdisperse or molecular disperse form, and is a biologically active ingredient selected from the group consisting of pharmaceutical active ingredients for humans and animals for orally administrable formulations.

2. The solid dispersion of claim 1, wherein the polymer matrix comprises a cationic copolymer of N,N-diethylaminoethyl methacrylate and methyl methacrylate in a weight ratio of the monomers of 45:55.

3. The solid dispersion of claim 1, comprising 20 to 50% by weight of the hydrophobic active ingredient.

4. The solid dispersion of claim 1, further comprising pharmaceutical additives.

5. The solid dispersion of claim 1, further comprising plasticizers.

6. A process for preparing the solid dispersion of claim 1, wherein a liquid mixture comprising the hydrophobic active ingredient, the antioxidant, and the cationic copolymer is prepared and the liquid mixture is converted to the solid form.

7. The process of claim 6, wherein the liquid mixture is present in the form of a solution or a melt.

8. The process of claim 6, wherein the conversion of the liquid mixture to the solid form is undertaken by spray-drying.

9. The process of claim 6, wherein the liquid mixture is prepared in a screw extruder with heating and, after extrusion, is solidified by cooling.

10. The process of claim 6, wherein the conversion to the solid form is undertaken by molding the liquid mixture to give a film and solidifying the film.

11. The process of claim 6, wherein the cationic copolymer is used in partially neutralized form.

12. The process of claim 6, wherein the cationic copolymer used is partially neutralized to 2 to 15 mol %, based on the cationic groups.

13. The process of claim 6, wherein the cationic copolymer used is partially neutralized with a C3-C10-dicarboxylic acid.

14. A method of preparing pharmaceutical dosage forms, the method comprising using the solid dispersion of claim 1 in pharmaceutical, cosmetic, agrochemical preparations, dietetic preparations, or in preparations of food supplements.

15. The solid dispersion of claim 1, wherein the hydrophobic active ingredient is a pharmaceutical active ingredient.

16. The solid dispersion of claim 1, wherein the hydrophobic active ingredient is not talc.

* * * * *